(12) United States Patent
Brouard et al.

(10) Patent No.: US 10,961,580 B2
(45) Date of Patent: Mar. 30, 2021

(54) METHODS FOR PREDICTING GRAFT ALTERATIONS

(71) Applicants: INSERM (Institut National de la Santé et de la Recherche Médicale), Paris (FR); Université de Nantes, Nantes (FR); Centre Hospitalier Universitaire de Nantes, Nantes (FR)

(72) Inventors: Sophie Brouard, Nantes (FR); Magali Giral, Nantes (FR); Richard Danger, Nantes (FR)

(73) Assignees: INSERM (Institut National de la Santé et de la Recherche Médicale), Paris (FR); Université de Nantes, Nantes (FR); Centre Hospitalier Universitaire de Nantes, Nantes (FR)

( * ) Notice: Subject to any disclaimer, the term of this patent is extended or adjusted under 35 U.S.C. 154(b) by 345 days.

(21) Appl. No.: 15/537,337

(22) PCT Filed: Dec. 18, 2015

(86) PCT No.: PCT/EP2015/080423
§ 371 (c)(1),
(2) Date: Jun. 16, 2017

(87) PCT Pub. No.: WO2016/097259
PCT Pub. Date: Jun. 23, 2016

(65) Prior Publication Data
US 2017/0342494 A1 Nov. 30, 2017

(30) Foreign Application Priority Data
Dec. 19, 2014 (EP) .................................. 14307111

(51) Int. Cl.
C12Q 1/68 (2018.01)
C12P 19/34 (2006.01)
C12Q 1/6883 (2018.01)
G01N 33/50 (2006.01)

(52) U.S. Cl.
CPC .......... *C12Q 1/6883* (2013.01); *G01N 33/502* (2013.01); *C12Q 2600/106* (2013.01); *C12Q 2600/118* (2013.01); *C12Q 2600/158* (2013.01); *C12Q 2600/16* (2013.01)

(58) Field of Classification Search
CPC ........ C12Q 2600/158; C12Q 2600/106; C12Q 2600/112; C12Q 2600/118; G01N 33/502
See application file for complete search history.

(56) References Cited

FOREIGN PATENT DOCUMENTS

| EP | 1850130 A1 | 10/2007 |
|---|---|---|
| WO | 2004018710 | 3/2004 |
| WO | 2005054503 | 6/2005 |
| WO | 2007104537 | 9/2007 |
| WO | 2010070043 | 6/2010 |
| WO | 2014074501 | 5/2014 |

OTHER PUBLICATIONS

Bohne, F. et al. Intra-graft expression of genes involved in iron homeostasis predicts the development of operational tolerance in human liver transplantation. J Clin Invest. 2012;122(1):368-382. (Year: 2012).*
Cheung, V.G. et al. "Natural variation in human gene expression assessed in lymphoblastoid cells" Nature Genetics, vol. 33, Mar. 2003, pp. 423-425 (Year: 2003).*
Chen, G. et al. Discordant Protein and mRNA Expression in Lung Adenocarcinomas Molecular & Cellular Proteomics 1.4, 2002, pp. 304-313 (Year: 2002).*
Cobb, J. P. et al. "Sepsis gene expression profiling: Murine splenic compared with hepatic responses determined by using complementary DNA microarrays" Crit Care Med 2002 vol. 30, No. 12 (Year: 2002).*
Hoshikawa, Y. et al. "Hypoxia induces different genes in the lungs of rats compared with mice" Physiol Genomics 12: 209-219, 2003 (Year: 2003).*
Chen et al., "Enrichr: interactive and collaborative HTML5 gene list enrichment analysis tool". BMC Bioinformatics. Apr. 15, 2013;14:128.
Condamine et al., "Tmem176B and Tmem176A are associated with the immature state of dendritic cells". J Leukoc Biol. Sep. 2010;88(3):507-15.
Cosio et al., "Predicting subsequent decline in kidney allograft function from early surveillance biopsies". Am J Transplant. Oct. 2005;5(10):2464-72.
Flechner et al., "Kidney transplant rejection and tissue injury by gene profiling of biopsies and peripheral blood lymphocytes". Am J Transplant. Sep. 2004;4(9):1475-89.
Furness et al., "Protocol biopsy of the stable renal transplant: a multicenter study of methods and complication rates". Transplantation. Sep. 27, 2003;76(6):969-73.
Günther et al., "Functional genomic analysis of peripheral blood during early acute renal allograft rejection". Transplantation. Oct. 15, 2009;88(7):942-51.
International Search Report of PCT application PCT/EP2015/080423, mailed by the EP Patent Office acting as the ISA on Feb. 2, 2016.
Loupy et al., "Outcome of subclinical antibody-mediated rejection in kidney transplant recipients with preformed donor-specific antibodies". Am J Transplant. Nov. 2009;9(11):2561-70.
Maluf et al., "Molecular pathways involved in loss of kidney graft function with tubular atrophy and interstitial fibrosis". Mol Med. May-Jun. 2008;14(5-6):276-85.

(Continued)

*Primary Examiner* — Stephen T Kapushoc
(74) *Attorney, Agent, or Firm* — Klarquist Sparkman, LLP

(57) ABSTRACT

The invention relates to a method for predicting graft alterations in a transplanted patient, comprising a step of determining the expression levels of bactericidal/permeability-increasing protein (BPI), chemokine (C motif) ligand 1 (XCL1) and thioredoxin domain containing 3 (TXNDC3) genes in a biological sample obtained from said transplanted patient.

8 Claims, 3 Drawing Sheets

(56) References Cited

OTHER PUBLICATIONS

Figure 1:
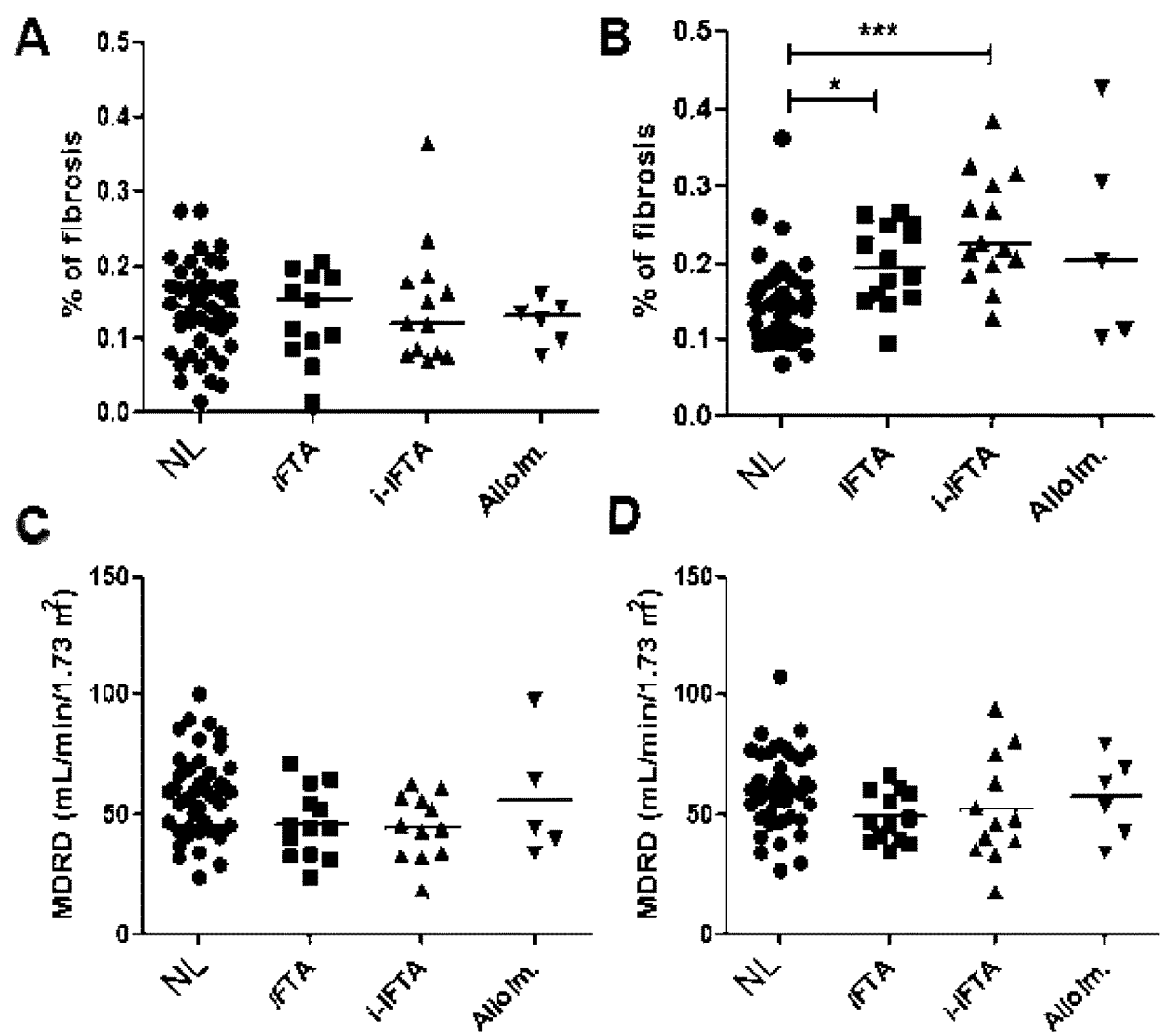

Mannon et al., "Inflammation in areas of tubular atrophy in kidney allograft biopsies: a potent predictor of allograft failure". Am J Transplant. Sep. 2010;10(9):2066-73.

Meas-Yedid et al., "New computerized color image analysis for the quantification of interstitial fibrosis in renal transplantation". Transplantation. Oct. 27, 2011;92(8):890-9.

Mengel et al., "Molecular correlates of scarring in kidney transplants: the emergence of mast cell transcripts". Am J Transplant. Jan. 2009;9(1):169-78.

Mengel et al., "Scoring total inflammation is superior to the current Banff inflammation score in predicting outcome and the degree of molecular disturbance in renal allografts". Am J Transplant. Aug. 2009;9(8):1859-67.

Mengel et al., "The molecular phenotype of 6-week protocol biopsies from human renal allografts: reflections of prior injury but not future course". Am J Transplant. Apr. 2011;11(4):708-18.

Naesens et al., "Progressive histological damage in renal allografts is associated with expression of innate and adaptive immunity genes". Kidney Int. Dec. 2011;80(12):1364-76.

Nankivell et al., "The natural history of chronic allograft nephropathy". N Engl J Med. Dec. 11, 2003;349(24):2326-33.

Park et al., "Fibrosis with inflammation at one year predicts transplant functional decline". J Am Soc Nephrol. Nov. 2010;21(11):1987-97.

Sarwal et al., "Molecular heterogeneity in acute renal allograft rejection identified by DNA microarray profiling". N Engl J Med. Jul. 10, 2003;349(2)125-38.

Scherer et al., "Early prognosis of the development of renal chronic allograft rejection by gene expression profiling of human protocol biopsies". Transplantation. Apr. 27, 2003;75(8):1323-30.

Scherer et al., "Transcriptome changes in renal allograft protocol biopsies at 3 months precede the onset of interstitial fibrosis/tubular atrophy (IF/TA) at 6 months". Nephrol Dial Transplant. Aug. 2009;24(8):2567-75.

Scian et al., "Gene expression changes are associated with loss of kidney graft function and interstitial fibrosis and tubular atrophy: diagnosis versus prediction". Transplantation. Mar. 27, 2011;91(6):657-65.

Segovia et al., "Autologous dendritic cells prolong allograft survival through Tmem176b-dependent antigen cross-presentation". Am J Transplant. May 2014;14(5):1021-1031.

Sellarés et al., "Inflammation lesions in kidney transplant biopsies: association with survival is due to the underlying diseases". Am J Transplant. Mar. 2011;11(3):489-99.

Serón et al., "Early protocol renal allograft biopsies and graft outcome". Kidney Int. Jan. 1997;51(1):310-6.

Sis et al., "Banff '09 meeting report: antibody mediated graft deterioration and implementation of Banff working groups". Am J Transplant. Mar. 2010;10(3):464-71.

Thaunat et al., "To biopsy or not to biopsy? Should we screen the histology of stable renal grafts?". Transplantation. Sep. 27, 2007;84(6):671-6.

Viklicky et al., "B-cell-related biomarkers of tolerance are up-regulated in rejection-free kidney transplant recipients". Transplantation. Jan. 15, 2013;95(1):148-54.

Villeda et al., "Young blood reverses age-related impairments in cognitive function and synaptic plasticity in mice". Nat Med. Jun. 2014;20(6):659-63.

Vitalone et al., "Transcriptome changes of chronic tubulointerstitial damage in early kidney transplantation". Transplantation. Mar. 15, 2010;89(5):537-47.

Zeeberg et al., "GoMiner: a resource for biological interpretation of genomic and proteomic data". Genome Biol. 2003;4(4):R28.

Zhang et al., "The clinical implication of inhibiting platelet activation on chronic renal allograft dysfunction: a prospective cohort study". Transplant Proc. Sep. 2011;43(7):2596-600.

\* cited by examiner

METHODS FOR PREDICTING GRAFT ALTERATIONS

CROSS REFERENCE TO RELATED APPLICATIONS

This is the U.S. National Stage of International Application No. PCT/EP2015/080423, filed Dec. 18, 2015, which was published in English under PCT Article 21(2), which in turn claims the benefit of European Patent Application No. 14307111.6, filed Dec. 19, 2014; which is incorporated herein in its entirety.

FIELD OF THE INVENTION

The invention relates to the field of medicine, and more particularly to the prediction of graft alterations (e.g. in kidney transplanted patients).

BACKGROUND OF THE INVENTION

Histological analysis is a useful tool in the detection and diagnosis of renal allograft injuries and one-year surveillance biopsies are regularly performed[1]. However, they indicate already established graft alterations and biomarkers established earlier, particularly from non-invasive procedures with less risk of complication, would provide physicians additional means to better adjust patient care as early as possible.

Interstitial Fibrosis and Tubular Atrophy (IFTA) is a common histological feature with no specific aetiology that has been linked to progressive deterioration of renal function and decreased graft survival[2]. In addition, the presence of fibrosis and inflammation has been shown to be associated with reduced graft function and survival[3-5] as early as in 1-year protocol biopsies[6], reinforcing the need of earlier biomarkers.

Using gene microarrays, several groups reported that it is possible to identify gene modulations in biopsies as early as 3 months post-transplantation[7, 8]. However, biopsy is invasive, and subject to complications and sampling errors, and histological analyses can exhibit significant variability in interpretation[9, 10]. Blood has been shown to be a useful compartment to observe gene expression modification associated with graft alterations within a context of acute renal allograft rejection[11, 12], but blood phenotype and/or gene expression patterns at 3 months post-transplant have never been studied nor suggested as useful for predicting the histological features of 12-month surveillance biopsies.

It would however be very useful to have a method to predict, without any previous modification of the immunosuppressive treatment, the graft alterations and the eventual subsequent graft rejection. Although well known biological parameters are used by clinicians for the evaluation of renal function (creatinine and urea serum concentrations and clearance), these parameters are not sufficient for a precise diagnosis of tolerance or rejection and most importantly, have poor predictive values. Currently, only a biopsy of the grafted kidney allows, through the analysis of the presence or absence of several histological lesion types, for the precise evaluation of said grafted kidney functionality. However, a biopsy is an invasive examination, which is not without danger for the grafted organ, and is thus usually not performed on transplanted patients that have stable biological parameters values. In addition, the variability of the diagnosis, due to the subjectivity of the analysis, is a drawback of the histological examination of biopsies. A non-invasive accurate and reliable method of predicting graft alterations/lesions is thus needed.

In addition, in the case of many grafted organ, when the values of standard biological parameters allow for diagnostic of graft alteration graft alteration, the process is already in progress and, although it may in certain cases be stopped, the alterations that have been induced generally cannot be reversed. Moreover, to establish the diagnostic, a biopsy of the grafted organ is usually performed, which is, as stated before, not without danger. It would thus also be very valuable to have a non-invasive method allowing to determine whether transplanted patients are at risk of organ function deterioration at the earlier steps of the process, which would permit to adapt the immunosuppressive treatment and might in some cases prevent the chronic rejection process.

SUMMARY OF THE INVENTION

In a first aspect, the invention relates to an in vitro method for predicting graft alterations in a transplanted patient, comprising a step of determining the expression level of at least one gene selected from the group consisting of bactericidal/permeability-increasing protein (BPI), chemokine (C motif) ligand 1 (XCL1) and thioredoxin domain containing 3 (TXNDC3) genes in a biological sample obtained from said transplanted patient.

In a second aspect, the invention relates to a kit suitable for performing the methods of the invention, wherein said kit comprises means for measuring the expression levels of BPI, XCL1 and TXNDC3 genes.

In a third aspect, the invention relates to the use of a kit comprising means for measuring the expression levels of BPI, XCL1 and TXNDC3 genes for performing the methods of the invention.

In a fourth aspect, the invention relates to a method for adjusting the immunosuppressive treatment administered to a transplanted recipient following its transplantation, comprising the following steps of: (i) performing the methods for predicting graft alterations in a transplanted patient of the invention, and (ii) adjusting the immunosuppressive treatment.

DETAILED DESCRIPTION OF THE INVENTION

The invention addresses these needs, as it relates to methods useful in the early prediction of development and progression of graft alterations.

The inventors indeed analyzed the gene profile and cell phenotype of a prospective cohort of 79 first renal recipients separated in 4 groups according to the one year surveillance biopsy: without lesion (Normal histology; NL); isolated IFTA; IFTA with isolated inflammatory infiltrate within the scarred compartment only (i-atr>0)(i-IFTA); and features of alloimmune injury (ALLO). By a study carrying out gene expression microarrays and cell phenotype performed on blood mononuclear cells at 3 months post-transplantation for these 79 renal transplant patients, the inventors demonstrated that blood gene expression can discriminate patients with 1-year normal biopsy through an association of only 3 genes with an area under a ROC curve of 0.76 after bootstrap resampling validation.

The present results suggest that blood gene expression very early after transplantation can predict abnormal histological graft alteration at one year, for all categories of alteration (IFTA, i-IFTA and ALLO) compared with normal histology. Accordingly, the inventors have shown that blood gene expression at three months post-transplant may predict graft alteration at one year. This minimally invasive, early signature may improve our understanding of graft injury and could be useful for early diagnostic and adjustment of therapy before graft injury.

Definitions

Throughout the specification, several terms are employed and are defined in the following paragraphs.

As used herein, the term "bactericidal/permeability-increasing protein (BPI) gene" encodes a lipopolysaccharide binding protein of 456 amino acids that is part of the innate immune system (Entrez gene ID No 671). It is associated with human neutrophil granules and has bactericidal activity on gram-negative organisms. The term includes naturally occurring BPI and variants thereof. The naturally occurring human BPI protein has an aminoacid sequence as shown in UniProt Accession number P17213 and is encoded by the nucleic acid sequence provided in the GenBank database under accession number NM_001725.

As used herein, the term "chemokine (C motif) ligand 1 (XCL1) gene" encodes a small cytokine of 114 amino acids belonging to the XC chemokine family that is also known as lymphotactin (Entrez gene ID No 6375). The term includes naturally occurring XCL1 and variants thereof. The naturally occurring human XCL1 protein has an aminoacid sequence as shown in UniProt Accession number P47992 and is encoded by the nucleic acid sequence provided in the GenBank database under accession number NM_002995.

As used herein, the term "thioredoxin domain containing 3 (TXNDC3) gene" encodes a protein of 588 amino acids also known as spermatid-specific thioredoxin-2 (Sptrx-2) with an N-terminal thioredoxin domain and three C-terminal nucleoside diphosphate kinase (NDK) domains (Entrez gene ID No 51314). The term includes naturally occurring TXNDC3 and variants thereof. The naturally occurring human TXNDC3 protein has an aminoacid sequence as shown in UniProt Accession number Q8N427 and is encoded by the nucleic acid sequence provided in the GenBank database under accession number NM_016616.

As used herein, the term "gene" refers to a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, "determining" encompasses detecting or quantifying. Indeed, an expression level can be qualitative or quantitative. Thus, a determination of whether a polynucleotide or polypeptide is present or absent (e.g., detectable or undetectable) constitutes determining its expression level in various embodiments while in other embodiments, a quantitative level is determined. A single measurement can provide information about the level of expression, activity, or both. Thus, evaluating the expression level of a protein includes evaluating one or more parameters or features that provide information about the level of expression of the protein, the activity of the protein, or both.

As used herein, "detecting" means determining if BPI, XCL1 and/or TXNDC3 is present or not in a biological sample and "quantifying" means determining the amount of BPI, XCL1 and/or TXNDC3 in a biological sample.

As used herein, the term "predetermined reference level" refers to the expression levels of BPI, XCL1 and TXNDC3 genes in biological samples obtained from the general population or from a selected population of subjects. For example, the selected population may be comprised of apparently healthy transplanted patient, such as individuals who have not previously had any sign or symptoms indicating the presence of graft alterations and/or outcome of a graft rejection. A "predetermined reference level" may be determined, for example, by determining the expression level of BPI, XCL1 and TXNDC3 nucleic acids or encoded polypeptides, in a corresponding biological sample obtained from one or more control subject(s) (e.g., not suffering from graft alteration and/or graft rejection or known not to be susceptible to such a disease). When such a predetermined reference level is used, a lower or decreased levels determined in a biological sample (i.e. a test sample obtained from the subject) is indicative for example that said patient is at risk of having graft alterations and/or graft rejection. The predetermined reference level may be established based upon comparative measurements between apparently healthy patients (e.g. patients classified with normal biopsy) and patients with established graft alterations (including IFTA, inflammatory IFTA and ALLO) and/or graft rejection (including chronic T-cell mediated rejection (c-TCMR) or chronic antibody-mediated rejection (c-ABMR)).

As used herein, a "lower" or "decreased" level refers to a expression level in a biological sample (i.e. blood sample obtained from the subject) which is at least 20% lower, in an embodiment at least 30% lower, in a further embodiment at least 40% lower; in a further embodiment at least 50% lower, in a further embodiment at least 100% lower (i.e. 2-fold), in a further embodiment at least 200% lower (i.e. 3-fold), in a further embodiment at least 300% lower (i.e. 4-fold), relative to the predetermined reference level (e.g., biological sample obtained from one or more control healthy patients (s)).

As used herein, the term "biological sample" refers to a biological sample obtained for the purpose of in vitro evaluation. In the methods of the invention, the biological sample may comprise any body fluid obtained from a patient. Typical biological samples to be used in the method according to the invention are blood samples (e.g. whole blood sample, serum sample, or plasma sample) and urine samples. A biological sample can be optionally pre-treated or processed prior to be used. Examples of pre-treatment steps include the addition of a reagent such as a stabilizer, a preservative, a fixant, a lysing reagent, a diluent, an anti-apoptotic reagent, a buffering reagent, an osmolarity regulating reagent, a pH regulating reagent, and/or a cross-linking reagent. Thus, a biological sample, can be analyzed under any of the methods and systems herein within 1 week, 6 days, 5 days, 4 days, 3 days, 2 days, 1 day, 12 hrs, 6 hrs, 3 hrs, 2 hrs, or 1 hr from the time the biological sample is obtained.

The term "transplantation" and variations thereof refers to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, including animals from phylogenically widely separated species.

In a first aspect, the invention relates to an in vitro method for predicting graft alterations in a transplanted patient, comprising a step of determining the expression level of at least one gene selected from the group consisting of bactericidal/permeability-increasing protein (BPI), chemokine (C motif) ligand 1 (XCL1) and thioredoxin domain containing 3 (TXNDC3) genes in a biological sample obtained from said transplanted patient.

As used herein, the term "graft alterations" refers to histological features according to the updated Banff classification 2009 and could be linked or not to progressive deterioration of graft function and survival. This term includes interstitial fibrosis and tubular atrophy (IFTA), inflammatory IFTA and alloimmune lesions (ALLO) gathering borderline changes, acute or chronic T-cell mediated rejection and acute or chronic antibody-mediated rejection (c-ABMR).

In one embodiment, the invention relates to an in vitro method for predicting graft alterations in a transplanted patient, comprising a step of determining the expression levels of BPI and XCL1 genes in a biological sample obtained from said transplanted patient.

In another embodiment, the invention relates to an in vitro method for predicting graft alterations in a transplanted patient, comprising a step of determining the expression levels of BPI and TXNDC3 genes in a biological sample obtained from said transplanted patient.

In another embodiment, the invention relates to an in vitro method for predicting graft alterations in a transplanted patient, comprising a step of determining the expression levels of XCL1 and TXNDC3 genes in a biological sample obtained from said transplanted patient.

In a preferred embodiment, the invention relates to an in vitro method for predicting graft alterations in a transplanted patient, comprising a step of determining the expression levels of BPI, XCL1 and TXNDC3 genes in a biological sample obtained from said transplanted patient.

In one embodiment, said method comprises a step of (i) determining the expression level of at least one gene selected from the group consisting of BPI, XCL1 and TXNDC3 genes in a biological sample obtained from said patient, and (ii) comparing said expression level with the respective predetermined reference level, wherein an decrease in the expression level of at least one said genes is predictive of graft alterations.

The predetermined reference value can be a threshold value or a range. A threshold value can also be arbitrarily selected based upon the existing experimental and/or clinical conditions, as would be recognized by a person of ordinary skilled in the art. For example, retrospective measurement of the expression level of the selected miRNA in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected mRNA in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. On the ROC curve, the point closest to the far upper left of the coordinate diagram is a critical point having both high sensitivity and high specificity values. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In one embodiment, the biological sample is a blood sample (e.g. whole blood sample, serum sample, or plasma sample) or a urine sample.

In a preferred embodiment, the biological sample is a blood sample.

In one embodiment, the biological sample is obtained 1-month post-transplantation, 2-months post-transplantation, 3-months post-transplantation, 4-months post-transplantation, 5-months post-transplantation or 6-months post-transplantation.

In a particular embodiment, the biological sample is a blood sample obtained 3-months post-transplantation.

In the setting of transplantation, it is envisioned that alterations of non-renal transplants would as well be predicted using the biomarkers of the invention. Accordingly, the invention also encompasses various types of transplants including, but not limited to, a renal allograft, a heart transplant, a lung allograft, a liver allograft or a pancreas allograft.

In one embodiment, the transplanted patient is a transplanted renal patient.

In one embodiment, said method comprises a step of (i) determining the expression level of at least one gene selected from the group consisting of BPI, XCL1 and TXNDC3 genes in a biological sample obtained from said patient, and (ii) comparing said expression level with the respective predetermined reference level, wherein an decrease in the expression level of at least one said genes is predictive of graft alterations.

The predetermined reference value can be a threshold value or a range as described above.

In the setting of transplantation, it is envisioned that alterations of non-renal transplants would as well be predicted using the biomarkers of the invention. Accordingly, the invention also encompasses various types of transplants including, but not limited to, a renal allograft, a heart transplant, a lung allograft, a liver allograft or a pancreas allograft.

In one embodiment, the transplanted patient is a transplanted renal patient.

In one embodiment, the biological sample is a blood sample (e.g. whole blood sample, serum sample, or plasma sample) or a urine sample.

In one embodiment, the biological sample is a blood sample (e.g. whole blood sample, serum sample, or plasma sample) or a urine sample.

In one embodiment, the biological sample is obtained 1-month post-transplantation, 2-months post-transplantation, 3-months post-transplantation, 4-months post-transplantation, 5-months post-transplantation or 6-months post-transplantation.

In a particular embodiment, the biological sample is a blood sample obtained 3-months post-transplantation.

Methods for Determining the Expression Level of the Biomarkers of the Invention:

Determination of the expression level of BPI, XCL1 and/or TXNDC3 genes gene may be performed by a variety of techniques. Generally, the expression level as determined is a relative expression level. For example, the determination comprises contacting the biological sample with selective reagents such as probes or ligands, and thereby detecting the presence, or measuring the amount, of nucleic acids or polypeptides of interest originally in said biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a particular embodiment, the expression level of the BPI, XCL1 and/or TXNDC3 genes may be determined by determining the quantity of mRNA.

Methods for determining the quantity of mRNA are well known in the art. For example the nucleic acid contained in the biological samples (e.g., peripheral blood mononuclear cells (PBMC) isolated from a blood sample obtained from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous.

Nucleic acids having at least 10 nucleotides and exhibiting sequence complementarity or homology to the mRNA of interest herein find utility as hybridization probes. It is understood that such nucleic acids need not be identical, but are typically at least about 80% identical to the homologous region of comparable size, more preferably 85% identical and even more preferably 90-95% identical. Probes typically comprise single-stranded nucleic acids of between 10 to 1000 nucleotides in length, for instance of between 10 and 800, more preferably of between 15 and 700, typically of between 20 and 500. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA.

It will be advantageous to use nucleic acids in combination with appropriate means, such as a detectable label, for detecting hybridization. A wide variety of appropriate indicators are known in the art including, fluorescent, radioactive, enzymatic or other ligands.

Conventional methods and reagents for isolating RNA from a sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

In one embodiment, the expression level of one or more mRNAs is determined by the quantitative polymerase chain reaction (QPCR) technique. The QPCR may be performed using chemicals and/or machines from a commercially available platform. The QPCR may be performed using QPCR machines from any commercially available platform; such as Prism, geneAmp or StepOne Real Time PCR systems (Applied Biosystems), LightCycler (Roche), RapidCycler (Idaho Technology), MasterCycler (Eppendorf), Bio-Mark™ HD System (Fluidigm), iCycler iQ system, Chromo 4 system, CFX, MiniOpticon and Opticon systems (Bio-Rad), SmartCycler system (Cepheid), RotorGene system (Corbett Lifescience), MX3000 and MX3005 systems (Stratagene), DNA Engine Opticon system (Qiagen), Quantica qPCR systems (Techne), InSyte and Syncrom cycler system (BioGene), DT-322 (DNA Technology), Exicycler Notebook Thermal cycler, TL998 System (lanlong), Line-Gene-K systems (Bioer Technology), or any other commercially available platform. The QPCR may be performed using chemicals from any commercially available platform, such as NCode EXPRESS qPCR or EXPRESS qPCR (Invitrogen), Taqman or SYBR green qPCR systems (Applied Biosystems), Real-Time PCR reagents (Eurogentec), iTaq mix (Bio-Rad), qPCR mixes and kits (Biosense), and any other chemicals, commercially available or not, known to the skilled person. The QPCR reagents and detection system may be probe-based, or may be based on chelating a fluorescent chemical into double-stranded oligonucleotides.

The QPCR reaction may be performed in a tube; such as a single tube, a tube strip or a plate, or it may be performed in a microfluidic card in which the relevant probes and/or primers are already integrated.

In a particular embodiment, the expression level of BPI, XCL1 and/or TXNDC3 genes may be determined by determining of the quantity of protein encoded by the BPI, XCL1 and/or TXNDC3 genes.

Such methods comprise contacting the biological sample with a binding partner capable of selectively interacting with the protein present in said sample. The binding partner is generally an antibody that may be polyclonal or monoclonal, preferably monoclonal.

Monoclonal antibodies directed against human BPI are well known from the skilled man in the art such as the antibodies commercialized by Pierce Antibodies (MA1-4012).

Monoclonal antibodies directed against human XCL1 are well known from the skilled man in the art such as the antibodies commercialized by Abnova (H00006375-M01).

Monoclonal antibodies directed against TXNDC3 are well known from the skilled man in the art such as the antibodies commercialized by Abnova (H00051314-M01).

As used herein, the term "monoclonal antibody" refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the invention.

Laboratory methods for preparing monoclonal antibodies are well known in the art (see, for example, Harlow et al., 1988). Monoclonal antibodies (mAbs) may be prepared by immunizing purified protein of the invention into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or lndocyanine (Cy5)) to the antibody or aptamer, as well as indirect labelling of the probe or antibody by reactivity with a detectable substance. An antibody or aptamer of the invention may be labelled with a radioactive molecule by any method known in the art.

The aforementioned assays generally involve the coating of the binding partner (ie. antibody or aptamer) in a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In another embodiment of the invention, the measurement of the biomarkers in the biological sample may be achieved by a cytometric bead array system wherein the antibodies that bind to the biomarkers are coated directly or indirectly on beads.

For example, the level of a biomarker protein such as BPI, XCL1 and/or TXNDC3 may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; Immunoelectrophoresis; immunoprecipitation, More particularly, an ELISA method can be used, wherein the wells of a microtiter plate are coated with a set of antibodies against BPI, XCL1 and/or TXNDC3. A biological sample containing or suspected of containing BPI, XCL1 and/or TXNDC3 is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Measuring the level of a biomarker protein such as BPI, XCL1 and/or TXNDC3 (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, Furin or a Furin substrate may be identified based on the known "separation profile" e.g., retention time, for that protein and measured using standard techniques.

Alternatively, the separated proteins may be detected and measured by, for example, a mass spectrometer.

Kits of the Invention

The invention also relates to a kit suitable for performing the methods of the invention, wherein said kit comprises means for measuring the expression levels of at least one gene selected from the group consisting of BPI, XCL1 and TXNDC3 genes.

In one embodiment, said means for measuring the expression levels of BPI, XCL1 and TXNDC3 genes are nucleic acid primers and/or probes specific for said genes.

The invention also relates to reagents, systems and kits thereof for practicing one or more of the above-described methods. The subject reagents, systems and kits thereof may vary greatly. Typically, the systems and kits of the invention include probes, primers macroarrays or microarrays as above described. For example, the kit may comprise a set of mRNA probes as above defined, usually made of DNA, and that may be pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards. Alternatively the kit of the invention may comprise amplification primers (e.g. stem-loop primers) that may be pre-labelled or may contain an affinity purification or attachment moiety. The kit may further comprise amplification reagents and also other suitably packaged reagents and materials needed for the particular amplification protocol. The systems and kits may further include one or more additional reagents employed in the various methods such as, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. labeled secondary antibodies, streptavidin-alkaline phosphatase conjugate, chemifluorescent or chemiluminescent substrate, and the like. In addition to the above components, the kit of the invention may further include instructions for practicing the methods of the present invention. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The invention also relates to a kit comprising means for measuring the expression levels of at least one gene selected from the group consisting BPI, XCL1 and TXNDC3 genes for performing the methods of the invention.

In a particular embodiment, said means for measuring the expression levels of BPI, XCL1 and TXNDC3 genes are nucleic acid primers and/or probes specific for said genes.

Methods for Adjusting an Immunosuppressive Treatment

The invention further provides methods for developing personalized treatment plans. Information gained by way of the methods described above can be used to develop a personalized treatment plan for a transplant recipient.

Accordingly, in a further aspect, the invention relates to a method for adjusting the immunosuppressive treatment administered to a transplanted patient following its transplantation, comprising the following steps of: (i) the methods for predicting graft alterations in a transplanted patient and (ii) adjusting the immunosuppressive treatment.

The methods can be carried out by, for example, using any of the methods for determining risk described above and, in consideration of the results obtained, designing a treatment plan for the transplant recipient. If the patient is at risk for an undesirable clinical outcome (e.g., graft alterations and/or graft rejection), said patient is a candidate for treatment with an effective amount of another immunosuppressive treatment that those administered since the transplantation (e.g. by an anti-rejection agent). Reducing the graft alterations such as fibrosis and/or protecting the allograft may be achieved using any suitable medical means known to those skilled in the art. Indeed, some immunosuppressive drugs are known as inducing fibrosis such as for instance inhibitors of calcineurin (e.g. cyclosporin).

In one embodiment, the step of adjusting the immunosuppressive treatment consists of modulating the amount administered to the transplanted patient and/or administering another immunosuppressive drug.

In a particular embodiment, said another immunosuppressive is an mTOR inhibitor (e.g. Sirolimus, Everolimus) which can be used in selected transplanted patient, where calcineurin inhibitors (Cyclosporin) are contraindicated.

In a particular embodiment, the transplanted patient is a transplanted renal patient.

The invention will be further illustrated by the following figures and examples. However, these examples and figures should not be interpreted in any way as limiting the scope of the present invention.

FIGURES

FIG. 1: Quantification of interstitial fibrosis using an automated image analysis pre-(A) and 1-year post-transplantation (B) and eGFR with MDRD formula 3 months post-transplantation (C) and at 1 year post transplantation (D).

Figure 2:
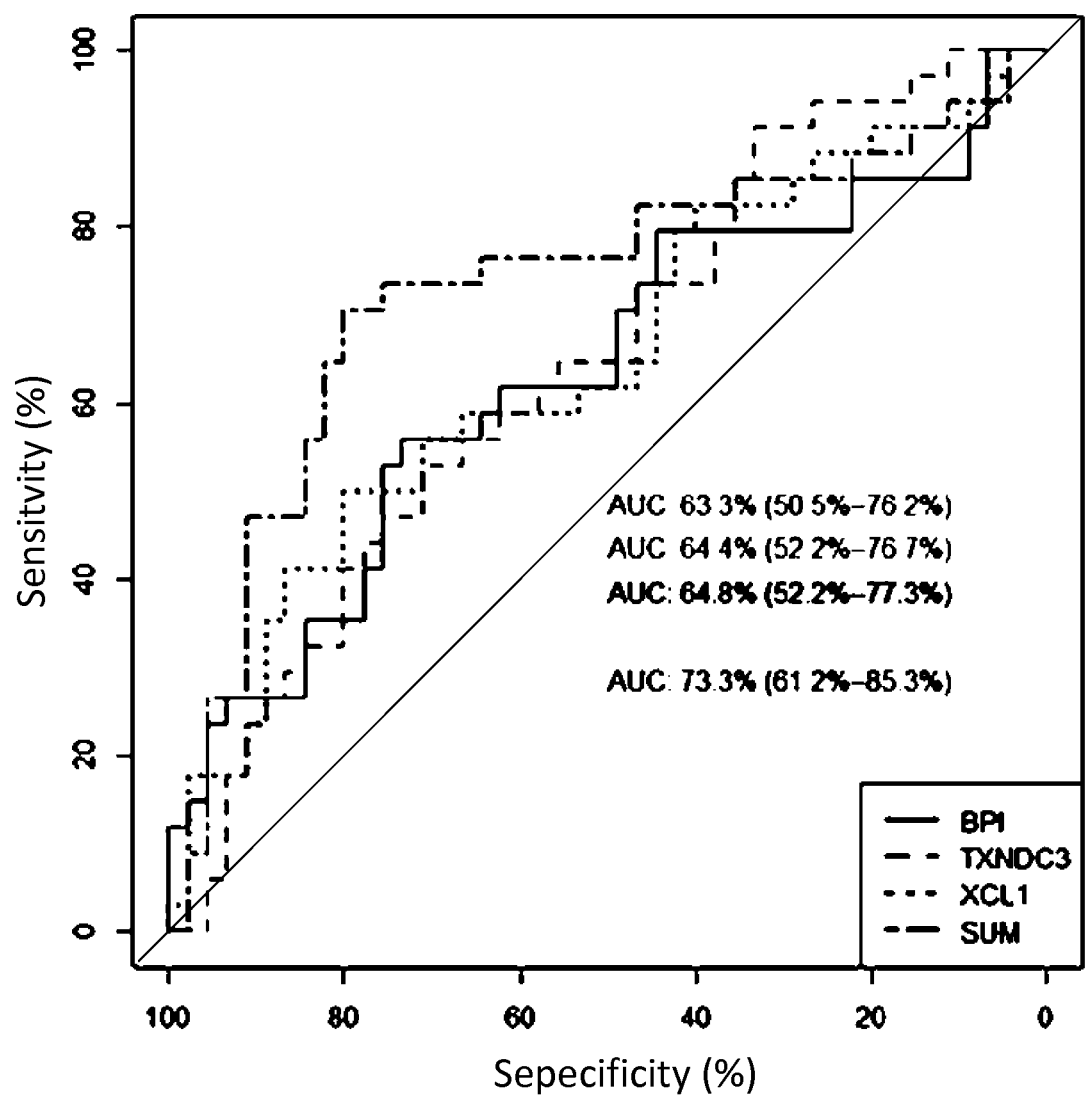

FIG. 2: ROC curves comparing NL group to the others combined. BPI, TXNDC3, XCL1 and the sum of values for these three genes exhibit significant discrimination (p=0.043, 0.029, 0.025 and 0.00015, respectively).

Figure 3:
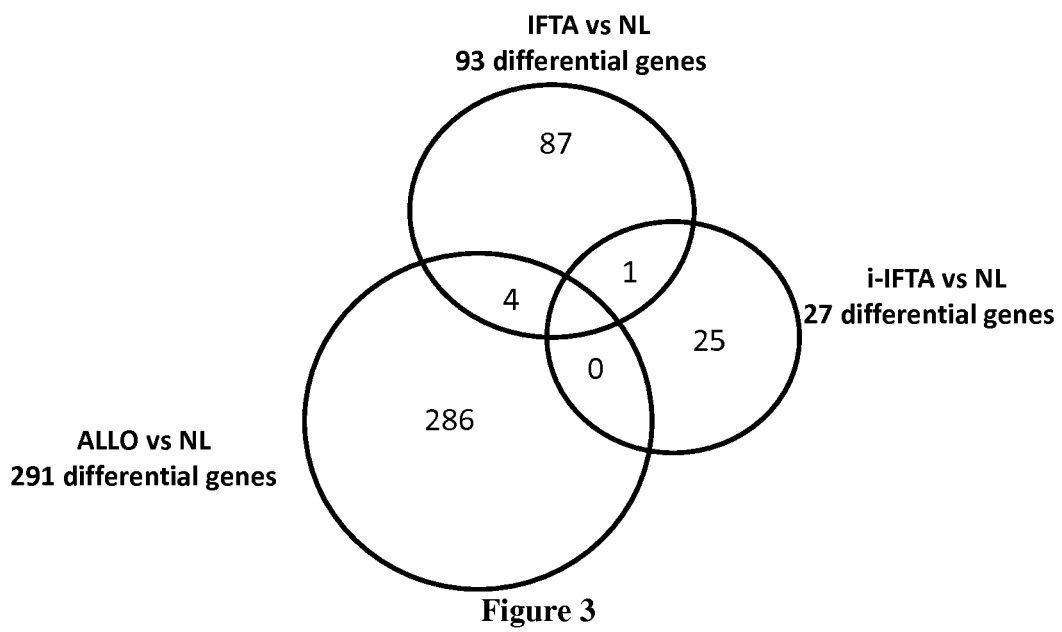

FIG. 3: Venn diagram of differential genes for each group compared to NL. The number of differential genes for each comparison is displayed with the overlap.

Figure 4:
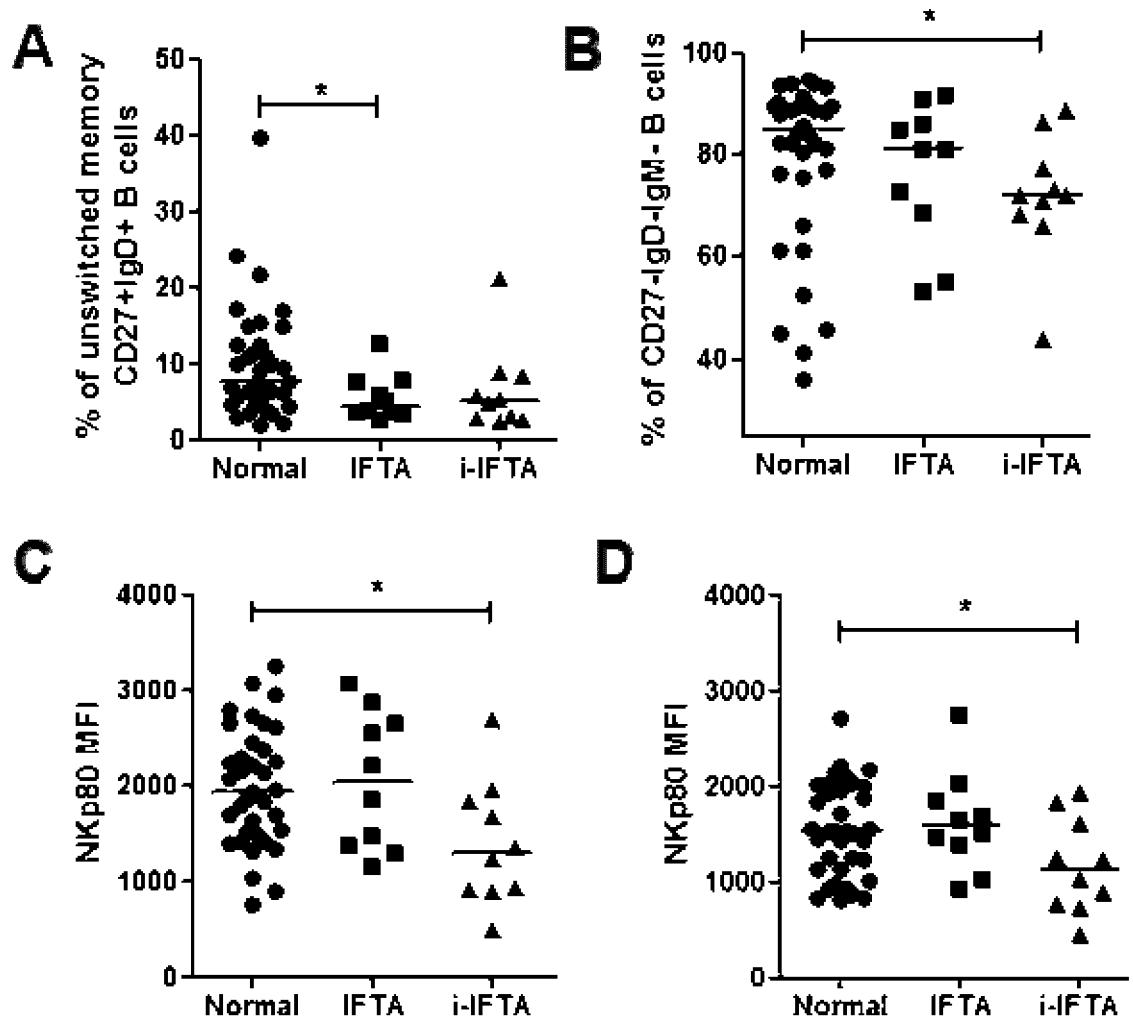

FIG. 4: Blood phenotype displaying significant differential subsets compared to the NL group.

EXAMPLE

Blood Gene Expression at 3 Months Post-Transplantation Predicts 1-Year Histological Features in Renal Transplantation Material & Methods Concise Methods Patients: A multicentre cohort of 79 renal transplant patients were analyzed in this study, given a grant by the French Health Ministry (no id RCB: DGS2006/0200) and approved by the University Hospital Ethical Committee and the Committee for the Protection of Patients from Biological Risks of Nantes (France). All patients gave informed consent. Six French transplant centers participated to the study (Nantes, Paris-Necker, Lyon-Heriot, Grenoble, Toulouse and Nice). Inclusion criteria were: adult patients under 66 years old who received a first isolated kidney transplantation from a heart-beating deceased donor of less than 60 years old.

Histopathological Analyses:

Histological diagnostic was centralized and performed according to the updated Banff classification 2009 [13] by 2 pathologists (K. R. and J. P. D. V. H.) blinded to the blood signatures. Pre and 1-year post-transplantation biopsies were assessed. Patients were classified in the 4 following groups: 1) normal, 2) isolated IFTA without inflammation (IFTA), 3) isolated IFTA with inflammation (i-IFTA), 4) alloimmune lesions (ALLO group) gathering borderline changes, acute or chronic T-cell mediated rejection and acute or chronic antibody-mediated rejection (c-ABMR). A diagnosis of isolated IFTA with or without inflammation (IFTA and i-IFTA) was given when no other patent histological associated lesion was observed and when the IFTA was not observed on the pre-implantation histology graft. The i-IFTA was defined by a ti-score>0 i.e. by the presence of interstitial inflammation on the scarred cortex area (i-atr) associated or not with inflammation in normal parenchyma (i-Banff) with an insufficient scoring to give a borderline change or T cell mediated rejection diagnosis (i-Banff=0 or 1)[27]. Patients with BK-virus nephropathy, as defined by the blood rate of virus replication by RT-PCR>4 log and renal dysfunction, were excluded from the study.

Blood Sample Preparation:

Venous blood samples were collected at 3 month post-transplantation in EDTA vacutainers and processed for analysis within 4 hours. Peripheral Blood Mononuclear Cells (PBMC) were separated on a Ficoll layer (Eurobio, Les Ulis, France). RNA was extracted from peripheral blood using the TRIzol method (Invitrogen, Cergy Pontoise, France).

Microarrays Analysis:

Analysis was performed on Affymetrix Human Genome U133 Plus 2.0 arrays. Microarray data from all samples were normalized using the robust multi-array algorithm (RMA) and a batch correction was performed with Combat algorithm according microarrays processed on Nantes and on the other centers data. A student test modified for multitesting (p-value <0.05) and a fold change of at least 1.25 were used to identify differentially expressed genes. The biological significance of selected genes was assessed using GOminer software[28]. Raw microarray data were deposited in the Gene Expression Ominbus (GEO) database and are accessible through GEO series accession number GSE57731.

Blood Phenotyping:

Flow cytometry was performed on a BD LSRII (BD Biosciences, Pont de Claix, France) and data were analyzed with FlowJo software (TriStar Inc, Ashland, Oreg., USA) using five combinations of monoclonal antibodies (mAb). All the experiments were performed on frozen PBMC.

Statistical analysis: non-parametric Mann-Whitney or Kruskal Wallis tests were used for group comparisons. Logistic regression was used to assess relationship between 12-months biopsy (NL versus other groups altogether) and co-variables. Statistical tests were done using R software. Graph PadPrism v.4 software (Graph Pad Prism Software, San Diego, Calif., USA) was used and differences were represented as follows: * when p<0.05,  when p<0.01 and * when p<0.001.

Results

Demographic Characteristics:

125 first-time kidney graft recipients were screened from which 79 fulfilled the complete one year follow-up with interpretable histology prior to graft implantation and at one year. Mean of age of recipients was 43.67 years ±SD: 10.47 (range: 20.10-63.0) with 73% male and mean donor age was 41.31±12.41 (12.0-65.0) with 61% male (table 1). The mean of HLA-A-B-DR incompatibility was 3.44±1.09 (0.0-5.0). All patients received Tacrolimus and mycophenolate mofetil. All patients received Basiliximab induction therapy except 2 who received rabbit thymoglobulin. Only 2 patients were free of steroids, one with diabetes and the other leucopoenia. No death occurred during the first year post-transplant, with an eGFR mean at one year of 57.14 mL/min/1.73 $m^2$±16.88 (17.71-108.0) and a daily proteinuria of 0.26 g/24 h±0.31 (0.0-2.0). Eight patients (10%) presented an acute rejection episode within the first year. At one year, 4 patients displayed DSA.

TABLE 1

Demographic characteristics of the cohort (A) and distribution of Banff criteria (B) (mean ±SD and range or percentages in brackets). P-value of Kruskal-Wallis test is indicated.

| A | All (n = 79) | NL (n = 45) | IFTA (n = 14) | iIFTA (n = 14) | ALLO (n = 6) | p-value |
|---|---|---|---|---|---|---|
| Estimated GFR at 3 months ± mL/min/1.73 $m^2$ | 53.65 ± 17.78 (18.39-100.0) | 58.04 ± 17.66 (23.87-100.0) | 46.34 ± 14.47 (24.12-71.51) | 45.09 ± 13.71 (18.39-63.10) | 56.34 ± 25.81 (34.46-97.80) | 0.082 |
| Estimated GFR at 1 year ± mL/min/1.73 $m^2$ | 57.14 ± 16.88 (17.71-108.0) | 60.91 ± 16.13 (26.56-108) | 49.00 ± 10.50 (35.35-66.60) | 52.40 ± 22.18 (17.71-94.36) | 57.23 ± 16.72 (34.41-79.03) | 0.071 |

TABLE 1-continued

Demographic characteristics of the cohort (A) and distribution of Banff criteria (B) (mean ±SD and range or percentages in brackets). P-value of Kruskal-Wallis test is indicated.

| | | | | | | |
|---|---|---|---|---|---|---|
| Proteinuria at 3 months ± g/24 h | 0.23 ± 0.17 (0.04-0.78) | 0.23 ± 0.19 (0.04-0.78) | 0.23 ± 0.15 (0.10-0.68) | 0.23 ± 0.17 (0.05-0.55) | 0.13 ± 0.08 (0.04-0.20) | 0.65 |
| Proteinuria at 1 year ± g/24 h | 0.26 ± 0.31 (0.0-2.0) | 0.22 ± 0.19 (0.0-0.97) | 0.20 ± 0.0.11 (0.09-0.41) | 0.45 ± 0.59 (0.04-0.36) | 0.18 ± 0.14 (0.04-0.36) | 0.94 |
| Male recipient | 55/75 (73%) | 29/43 (67%) | 11/13 (84%) | 11/13 (84%) | 4/6 (66%) | 0.072 |
| Recipient's age | 43.67 ± 10.47 (20.10-63.0) | 43.77 ± 11.01 (20.10-63.00) | 45.13 ± 10.86 (24.00-59.40) | 43.33 ± 10.20 (25.90-59.40) | 40.57 ± 7.382 (27.20-48.60) | 0.77 |
| Male donor | 44/72 (61%) | 26/41 (63%) | 8/13 (62%) | 8/12 (67%) | 2/6 (33%) | 0.57 |
| Donor's age | 41.31 ± 12.41 (12.00-65.00) | 41.10 ± 12.86 (12.00-65.00) | 44.31 ± 14.12 (20.00-61.00) | 37.83 ± 9.64 (20.00-50.00) | 43.17 ± 11.11 (29.00-54.00) | 0.49 |
| Recurrent disease | 19/75 (25.3%) | 13/42 (31.0%) | 3/13 (23.1%) | 2/14 (14.%) | 1/6 (16.7%) | 0.60 |
| HLA-ABDR missmatches | 3.44 ± 1.09 (0.0-5.0) | 3.43 ± 1.17 (0.0-5.0) | 3.31 ± 1.11 (1.0-4.0) | 3.50 ± 0.94 (1.0-5.0) | 3.67 ± 1.03 (2.0-5.0) | 0.95 |
| Basiliximab induction | 70/72 (97.2%) | 40/41 (97.6%) | 13/13 (100%) | 11/12 (91.7%) | 6/6 (100%) | nd |
| Tacrolimus use at initial treatment | 76/76 (100%) | 43/43 (100%) | 13/13 (100%) | 14/14 (100%) | 6/6 (100%) | nd |
| Corticosteroids | 70/72 (97.2%) | 40/41 (97.6%) | 13/13 (100%) | 11/12 (91.7%) | 6/6 (100%) | nd |
| DSA at 1 year | 4/73 (5.5%) | 2/41 (4.5%) | 0/14 (0%) | 1/12 (8.3%) | 1/6 (16.7%) | |
| ARE occurrence during the first year | 8/77 (10.4%) | 4/44 (9.1%) | 1/13 (7.7%) | 2/14 (14.3%) | 1/6 (16.7%) | nd |

| B | All (n = 79) | NL (n = 45) | IFTA (n = 14) | i-IFTA (n = 14) | ALLO (n = 6) | p-value | Significant comparison |
|---|---|---|---|---|---|---|---|
| g | 0.089 ± 0.33 (0-2) | 0.0 ± 0.0 (0-0) | 0.14 ± 0.36 (0-1) | 0.29 ± 0.0.61 (0-2) | 0.17 ± 0.0.41 (0-1) | 0.028 | NL vs IFTA: $p < 0.05$ |
| ptc | 0.053 ± 0.28 (0-2) | 0 ± 0 (0-0) | 0 ± 0 (0-0) | 0.15 ± 0.38 (0-1) | 0.33 ± 0.82 (0-2) | 0.028 | ns |
| i | 0.089 ± 0.33 (0-2) | 0.022 ± 0.15 | 0 ± 0 (0-0) | 0.14 ± 0.0.36 (0-1) | 0.67 ± 0.82 (0-2) | 0.002 | iIFTA vs ALLO: $p < 0.05$ NL vs ALLO: $p < 0.0001$ IFTA vs ALLO: $p < 0.0001$ |
| t | 0.20 ± 0.54 (0-2) | 0.044 ± 0.21 (0-1) | 0 ± 0 (-0) | 0.36 ± 0.63 (0-0) | 1.5 ± 0.84 (0-0) | $P < 0.0001$ | i-IFTA vs ALLO: $p < 0.0001$ NL vs ALLO: $p < 0.0001$ IFTA vs ALLO: $p < 0.0001$ |
| cg | 0 ± 0 (0-0) | 0 ± 0 (0-0) | 0 ± 0 (0-0) | 0 ± 0 (0-0) | 0 ± 0 (0-0) | | |
| ci | 0.66 ± 0.088 (0-3) | 0.13 ± 0.34 (0-1) | 1.07 ± 0.27 (1-2) | 1.43 ± 0.0.65 (1-3) | 1.83 ± 0.98 (1-3) | $P < 0.0001$ | NL vs IFTA: $p < 0.0001$ NL vs i-IFTA: $p < 0.000$ NL vs ALLO: $p < 0.0001$ |
| ct | 0.85 ± 0.72 (0-3) | 0.47 ± 0.50 (0-1) | 1.07 ± 0.27 (0-2) | 1.43 ± 0.65 (1-3) | 1.83 ± 0.98 (1-3) | $P < 0.0001$ | ±**: NL vs IFTA; ***: NL vs i-IFTA; ***: NL vs ALLO; |
| ti | 0.44 ± 0.68 (0-3) | 0.18 ± 0.39 (0-1) | 0 ± 0 | 1.07 ± 0.27 2) | 1.83 ± 0.98 (1-3) | | ±***: NL vs i-IFTA; ***: NL vs ALLO; ***: IFTA vs i-IFTA; ***: IFTA vs ALLO |

Demographic Characteristics According to Histological Features:

Histological analyses were performed on pre- and 1-year post-transplant biopsies for the 79 patients. Pre-implantation biopsies were used to exclude pre-existing features from the analysis i.e. only features appearing after transplantation are analyzed. Patients were classified into four categories following the 2009 Banff classification[13]: 45 patients were classified with normal biopsy (NL), 14 isolated IFTA without inflammation (IFTA), 14 isolated IFTA with inflammation (i-IFTA) and 6 presenting alloimmune lesions (ALLO), combining borderline changes, acute or chronic T-cell mediated rejection and acute or chronic antibody-mediated rejection (c-ABMR) (table 1). There was no functional difference between the 4 groups in estimated graft function (eGFR) using the MDRD formula either 3 months post-transplant, when blood samples were harvested for cell phenotype and microarrays analysis, or 1 year post-transplant when histology was performed (FIG. 1, table 1). However, patients with IFTA and i-IFTA displayed around 10 ml/min/1.72 m² lower eGFR at 3 months and one year than NL or ALLO patients. This difference is not statistically significant and maybe related to the sample size in each group. Finally, the ALLO immune group tended to have younger recipients than the other groups. Independent quantification of fibrosis using an automated image analysis procedure confirmed a significantly higher percentage of fibrosis 1-year post-transplantation in IFTA and i-IFTA patients compared to NL patients ($p<0.05$ and $p<0.001$, respectively), whereas no difference was observed at the time of transplantation (FIG. 1).

A 3-Month Blood Gene Signature for Normal Histology:

We first compared the blood gene expression of the patients with NL histology with all the other groups (IFTA, i-IFTA and ALLO) to assess whether gene expression in the blood at 3 months could be associated with "normal vs abnormal" histology at one year. Six genes were significantly differentially expressed between the NL group and the others (supplementary table 1). In addition, three of them, BPI (bactericidal/permeability-increasing protein), XCL1 (chemokine (C motif) ligand 1) and TXNDC3 (thioredoxin domain containing 3) exhibited significant area under the curve (AUC) in receiver operating characteristic analyses (ROC)(supplementary table 1) and the simple combination of these 3 markers, i.e the sum of expression values, allowed the differentiation of NL patients from others, with an AUC of 0.73 ($CI_{95\%}=[0.61, 0.85]$, $p=0.00015$) (FIG. 2). Exclusion of the 2 patients who received rabbit thymoglobulin induction and the 2 who were free of steroids resulted in a significant AUC of 0.77 ($CI_{95\%}=[0.65, 0.88]$, $p<0.0001$). In addition, univariate/multivariate analyses highlighted that 3-months eGFR (MDRD formula) and the sum of these three genes were significantly associated with prediction of 1-year biopsy status (Wald p-value=0.025 and 0.0085, respectively). When both parameters were combined, the accuracy of prediction improves with an AUC of 0.75 ($CI_{95\%}=[0.64, 0.87]$, $p<0.0001$) and a bootstrap resampling validation confirmed the stability of this composite biomarker displaying an AUC of 0.76 ($CI_{95\%}=[0.64, 0.86]$, $p<0.0001$).

SUPPLEMENTARY TABLE 1

6 genes significantly differential between normal group and others groups.

| Symbol | GeneName | Entrez | FC | p | ROC p-value | AUC | 95% IC AUC |
|---|---|---|---|---|---|---|---|
| GPR84 | G protein-coupled receptor 84 | 53831 | −1.33 | 0.044 | 0.073 | 0.62 | 0.49-0.74 |
| BPI | bactericidal/permeability-increasing protein | 671 | −1.45 | 0.039 | 0.043 | 0.63 | 0.51-0.76 |
| XCL1 | chemokine (C motif) ligand 1 | 6375 | −1.27 | 0.025 | 0.025 | 0.65 | 0.52-0.77 |
| LGALSL | lectin, galactoside-binding-like | 29094 | −1.28 | 0.043 | 0.066 | 0.62 | 0.50-0.75 |
| TXNDC3 | thioredoxin domain containing 3 (spermatozoa) | 51314 | −1.25 | 0.041 | 0.029 | 0.64 | 0.52-0.76 |
| BNIP3 | BCL2/adenovirus E1B 19kDa interacting protein 3 | 664 | 1.28 | 0.044 | 0.15 | 0.63 | 0.45-0.81 |

Gene Signatures Associated with 1-Year Histological Lesions: in order to identify blood specific gene signatures at three months associated with each histologic feature at one year, the three groups, IFTA, i-IFTA and ALLO, were compared separately to the NL group (FIG. 3). Ninety three genes (56 down- and 37 up-regulated) were differentially expressed between the IFTA and NL groups. Gene ontology (GO) analysis evidenced gene categories mainly related to cell homeostasis and coagulation/platelet function (table 2), such as integrins alpha 2b and beta 3 (CD41/CD61) and lectins (CLEC1B, -4A, -12A, -12B), which are down-expressed in IFTA compared to NL. Similarly, 27 genes (10 down- and 17 up-regulated) were differentially expressed between the i-IFTA and NL groups. Among these, we identified immune-related genes, such as the under-expressed genes CD8B, XCL1, IL31RA (interleukin 31 receptor A), MIR142 (microRNA 142) and the over-expressed genes CX3CR1 (chemokine (C-X3-C motif) receptor 1), KLRF1 (killer cell lectin-like receptor subfamily F, member 1), EGR1 (early growth response 1), TMEM1764A and TMEM176B (transmembrane proteins 176A and 176B). No significant GO enrichment was found between these two groups of patients, likely due to the too low number of genes. Finally, 291 genes (218 down- and 73 up-regulated) were differentially expressed between the ALLO and NL groups. As expected, GO analysis also highlighted significant enrichments of immune-related genes (table 3) with a total of 54 genes, among which genes coding for CD24 molecule, interleukin 1 receptors (type I, type II and antagonist (IL1R1, IL1R2, IL1R1N), metalloproteinase 8 and 9 (MMP8, MMP9) down-regulated in the ALLO group. Using the cell-type enrichment analysis form Enrichr database[14], we identified an enrichment of cell type transcripts related to CD33+ myeloid cells and CD14+ monocytes ($p<0.001$ and 0.004, respectively) in the ALLO group.

Altogether, we identified three distinct and significant differential gene signatures in blood at 3 months post-transplantation, associated with 1-year IFTA, i-IFTA and ALLO events with a gradient in favour of immunity related genes in the last group, suggesting that blood signature may be worth considering in clinic. Interestingly, only a small overlap was found between the signatures, reinforcing their specificity (FIG. 3).

TABLE 2

GO enrichment for the IFTA group compared to the NL. Only GO with false discovery rate (FDR) inferior to 5% were selected.

| | GO Category | GO Name | Total genes | Changed genes | Enrichment | FDR |
|---|---|---|---|---|---|---|
| 1 | GO: 0050896 | response to stimulus | 4180 | 36 | 2.0 | .001 |
| 2 | GO: 0046903 | secretion | 636 | 13 | 4.7 | .001 |
| 3 | GO: 0002576 | platelet degranulation | 82 | 6 | 16.8 | .001 |
| 4 | GO: 0030168 | platelet activation | 233 | 8 | 7.9 | 0.003 |
| 5 | GO: 0007608 | sensory perception of smell | 365 | 9 | 5.7 | 0.005 |
| 6 | GO: 0006887 | exocytosis | 222 | 7 | 7.2 | 0.008 |
| 7 | GO: 0007606 | sensory perception of chemical stimulus | 407 | 9 | 5.1 | .008 |
| 8 | GO: 0032940 | secretion by cell | 530 | 10 | 4.3 | 0.010 |
| 9 | GO: 0050878 | regulation of body fluid levels | 454 | 9 | 4.5 | 0.014 |
| 10 | GO: 0007599 | hemostasis | 386 | 8 | 4.8 | 0.023 |
| 11 | GO: 0006950 | response to stress | 2170 | 21 | 2.2 | 0.024 |
| 12 | GO: 0050817 | coagulation | 383 | 8 | 4.8 | 0.024 |
| 13 | GO: 0007596 | blood coagulation | 380 | 8 | 4.8 | 0.025 |
| 14 | GO: 0045595 | regulation of cell differentiation | 586 | 10 | 3.9 | 0.026 |
| 15 | GO: 0001775 | cell activation | 616 | 10 | 3.7 | 0.029 |
| 16 | GO: 0050793 | regulation of developmental process | 787 | 11 | 3.2 | 0.046 |

TABLE 3

GO enrichment for the ALLO group compared to the NL. Only GO with FDR inferior to 5% were selected.

| | GO Category | GO Name | Total genes | Changed genes | Enrichment | FDR |
|---|---|---|---|---|---|---|
| 1 | GO: 0002376 | immune system process | 1243 | 42 | 2.3 | 0.000 |
| 2 | GO: 0006952 | defense response | 773 | 31 | 2.7 | 0.000 |
| 3 | GO: 0006955 | immune response | 761 | 28 | 2.5 | 0.003 |
| 4 | GO: 0009617 | response to bacterium | 229 | 14 | 4.1 | 0.004 |
| 5 | GO: 0042742 | defense response to bacterium | 107 | 9 | 5.6 | 0.011 |
| 6 | GO: 0002444 | myeloid leukocyte mediated immunity | 29 | 5 | 11.6 | 0.019 |

Unique Enrichment of Differential Immune-Related Genes in IFTA, i-IFTA and ALLO Groups: IFTA and i-IFTA display, respectively, 93 and 27 genes that are differentially expressed at three months compared to the NL group. Among them, there were only 2 common genes (BAGE3 (B melanoma antigen family, member 3) and DNAJA1P5 (DnaJ (Hsp40) homolog, subfamily A, member 1 pseudogene 5)) (FIG. 3), suggesting different signatures between the two IFTA situations depending on the inflammatory component. To further ascertain this, IFTA and i-IFTA were directly compared and 258 genes were found to be differentially expressed. GO analysis and Enrichr database revealed an enrichment of 58 unique genes, some related to CD14+ monocytes, including over-expressed genes coding for immune-related molecules such as CD36, CD93, TLR5 (toll-like receptor 5) and CCR2 (chemokine (C—C motif) receptor 2) (table 4). Similarly, the i-IFTA and ALLO groups were directly compared and we found that, among the 291 differential genes associated with the ALLO group and the 27 associated with i-IFTA, only one gene, (BAGE3) was common to the two situations, stressing the idea that the cellular mechanisms and most overall immune mechanisms of alloimmune reactions and i-IFTA are distinct.

TABLE 4

GO enrichment for the i-IFTA group compared to the IFTA group. Only GO with a FDR inferior to 5% were selected.

| | GO Category | GO Name | Total genes | Changed genes | Enrichment | FDR |
|---|---|---|---|---|---|---|
| 1 | GO: 0001775 | cell activation | 616 | 27 | 3.3 | 0.000 |
| 2 | GO: 0002376 | immune system process | 1243 | 37 | 2.3 | 0.001 |
| 3 | GO: 0042116 | macrophage activation | 28 | 6 | 16.3 | 0.002 |
| 4 | GO: 0045321 | leukocyte activation | 402 | 18 | 3.4 | 0.002 |
| 5 | GO: 0002682 | regulation of immune system process | 595 | 22 | 2.8 | 0.004 |
| 6 | GO: 0002274 | myeloid leukocyte activation | 75 | 7 | 7.1 | 0.017 |
| 7 | GO: 0002237 | response to molecule of bacterial origin | 136 | 9 | 5.0 | 0.017 |
| 8 | GO: 0006952 | defense response | 773 | 24 | 2.4 | 0.020 |
| 9 | GO: 0032496 | response to lipopolysaccharide | 125 | 8 | 4.9 | 0.038 |
| 10 | GO: 0009617 | response to bacterium | 229 | 11 | 3.7 | 0.040 |
| 11 | GO: 0006950 | response to stress | 2170 | 47 | 1.6 | 0.041 |

Blood Phenotype Analysis: Peripheral Blood from the IFTA (n=10), i-IFTA (n=10) and NL Groups (n=36) were Analyzed at Three Months Following Transplantation Using Flow Cytometry. Comparison of the three groups together did not highlight any significant difference in cell frequency. Thus, no phenotype parameter was used to predict 1-year histology in association with gene expression. However, when IFTA was compared to the NL group only, the frequency of unswitched memory CD27+IgD+ B cells was significantly lower in the IFTA group (NL=7.70%, $CI_{95\%}$=[7.48, 12.49]; IFTA=4.48%, $CI_{95\%}$=[3.50, 7.84], p=0.047) (FIG. 4A). The i-IFTA group, compared to the NL group, was characterized by a lower CD27−IgD−IgM− double negative memory B cell frequency (NL=85.0%, $CI_{95\%}$=[73.34, 84.49]; i-IFTA=72.05%, $CI_{95\%}$=[63.15, 80.65], p=0.034) (FIG. 4B) and by a lower expression of NKp80 (MFI) on secretor (NL=1940, $CI_{95\%}$=[1773, 2192]; i-IFTA=1292, $CI_{95\%}$=[936.1, 1865], p=0.018) and transitional (p=0.043; NL=1532, $CI_{95\%}$=[1376, 1705]; i-IFTA=1137, $CI_{95\%}$[818.7, 1527]) NK cells compared to the NL group (FIG. 4C, 4D).

Altogether there is a lower frequency of unswitched memory B cells in IFTA and a decrease in double negative memory B cells and NKp80 expression on secretory and transitional NK cells in i-IFTA. No other modification was found at a cellular level.

DISCUSSION

Histological analysis of allograft biopsy remains the gold standard for assessing graft alterations. Several studies demonstrate that such alterations are associated with changes in transcript sets representing inflammation and injury in renal allografts[7, 8, 12, 15, 16]. The presence of histological lesions such as fibrosis and inflammation in 1-year protocol biopsies is associated with reduced graft function and survival[6]. However, biopsies can involve severe complications[9, 10].

We assessed gene expression and cell phenotype in blood from 79 first-time kidney recipients 3 months post-transplant compared with histological statuses one year post-transplantation surveillance biopsy with the aim of determining whether blood could be a valuable compartment for early prediction of graft alterations, reducing the risk of complication and providing tool for early decision-making. Consistent with the development of a predictive biomarker, i.e. before functional alteration, no change in renal function was observed in our cohort between 3 months and 1 year of follow-up. To reduce variability in lesion interpretation as much as possible, histological diagnostic was performed independently by 2 pathologists. Fibrosis quantification, using automated image analysis[17], confirmed the significant occurrence of fibrosis between the pre-implantation biopsy and the one-year surveillance biopsies in the IFTA and i-IFTA groups.

The comparison of patients with normal histology and the 3 groups of patients with abnormal histological features allowed the identification of 6 differentially expressed genes. The combination of 3 of them allows a good discrimination, with an AUC of 0.73 ($CI_{95\%}$=[0.61, 0.85], p=0.00015). This sum of expression of these 3 genes and the 3-months eGFR were found to be independent predictors of 12-month graft histology and their combination allows reaching a good discriminatory accuracy with an AUC of 0.76 ($CI_{95\%}$=[0.64, 0.86], p<0.0001) after bootstrap resampling validation. This composite biomarker gives a potential early, minimally invasive biomarker with good predictive ability to distinguish at 3-months post-transplantation patients who will exhibit abnormal biopsy 1 year after transplantation. The identification of predictive biomarkers raises the possibility to stratify patients, avoiding 1-year biopsy for patients predicted to have normal histology and adapting treatment. Such prophylactic treatment would also be of interest for patients with high-risk allografts, including those with a positive cross-match[18], who could benefit from early adjustments to their immunosuppressive regimens.

Our data confirm that blood is a good compartment, not only for identifying biomarkers associated with allograft injuries as previously reported in acute rejection[11, 12], but also for predicting histological lesions. In addition, because taking samples is minimally invasive and easily repeated, blood potentially represents an optimal and safe source for predictive biomarkers.

Our data also suggest that 3 months may be a good point for early detection of abnormal events. Indeed, Mengel and colleagues showed that gene expression analysis in 6-weeks protocol biopsies mostly reflected the injury-repair response to implantation stresses following transplantation[19]. This suggests that molecular events impacting allograft outcomes are initially hidden by tissue repair response, for example an initial increase in adaptive immune-associated genes 1 month post-transplantation is later reduced in a longitudinal analysis[20]. The stability of our signature over time needs to be investigated in order to define during which time lapse its sensitivity is optimal.

Compared to the NL group, the distinct histological features of the three other groups of patients are associated with specific gene signatures with coherent biological profiles and very little overlap. The ALLO group exhibits a clear signature of immune-related genes evidencing active immunologic processes and thus validating our transcriptional approach. The over-expression of CD24, a gene expressed in mature B cells, could be explained by the B and mast cell infiltration reported following inflammation whereas the over-expression of MMP8/9 genes fits with tissue remodeling occurring in injured tissue[5, 7, 21]. In contrast with the two other groups of patients, the i-IFTA group is associated with few differential genes compared with the NL group but these include genes related to the immune system: TMEM1764B (also called TORID) and its partner TMEM1764A were up-regulated in i-IFTA (FC=1.8 and 2.0, respectively). Interestingly, these two genes have been shown to play a role in dendritic cell maturation and are required for the presentation of donor antigens to $CD8^+$T cells[22, 23]. TMEM1764B and its partner TMEM1764A are also up-regulated in blood from kidney transplanted patients with acute rejection[24]. The presence of these genes in this particular situation fits with the increased macrophages/dendritic cell ($CD68^+$ cells) infiltrate observed in biopsies with fibrosis and signs of inflammation[6]. In contrast, several other molecules, mainly related to lymphocytes, were found to have a lower expression in i-IFTA, including CD8B, XCL1, IL31RA and MIR142, markers of migration and homing. This probably correlates to migration of blood lymphocytes towards the graft, as previously described in one-year biopsies with fibrosis and inflammation[6], which suggests that lymphocyte migration appears as soon as 3 months post-transplantation.

The IFTA group was associated with 93 differential genes compared with NL patients including some integrins and lectins and the enrichment of platelet and coagulation-related GO. The modulation of these genes coding for integrins may result from a blood cell adaptation induced by extracellular matrix modification in grafts with IFTA lesions as previously extensively described[7]. This fits with the fact that administration of platelet activation inhibitor delays fibrosis during chronic renal allograft dysfunction[25]. Interestingly, and contrasting with our results, IFTA has been reported to be associated with an increase in immune-related genes in biopsies[7, 16, 21]. However, in these studies, no distinction was made between patients with IFTA and those with i-IFTA, explaining why we only found differential immune-related genes in the blood from i-IFTA patients. For example, 16 out of 17 patients had an i-score equal to 2 or 3 in the IFTA group in Maluf et al., in our study, we would have classified these patients as i-IFTA[21].

Altogether, our results clearly suggest a lower expression of immune-related genes in periphery as a reflection of the graft infiltration in i-IFTA but not in IFTA biopsies. Interestingly, these data are in accordance with the blood phenotype of the patients. We found a lower frequency of $CD27^-IgD^-IgM^-$ double negative memory B cells and decreased expression of NKp80 on secretory and transitional NK cells in i-IFTA compared to the NL group. These data fit with a traffic of immune cells from the blood to the allograft, on the site of inflammation and particularly with the higher B-cell related infiltrate observed in i-IFTA[5].

Very few differential genes highlighted in recipient blood in this study have previously been reported in allograft biopsies. This is in accord with Flechner et al. who reported on very few common genes between circulating lymphocyte pool and biopsy in patients with well-functioning transplants or with acute rejection[12]. This may be due to compartment-specific cell localization and gene expression as well as movement of activated cells from the peripheral blood through the kidney, as described above.

In conclusion, while gene expression profiling in biopsy have been extensively reported to be associated with graft alteration, little attention has been paid to the patterns in periphery. Our study shows that gene expression in peripheral blood cells could predict which patients will have abnormal histology at 1-year post transplantation, allowing early adaptation of clinical management procedures prior to graft injury. These data suggest that blood may be a satisfactory compartment to indirectly predict graft outcome, reducing the risk of rejection and the need for hospitalization. It would thus be of interest to integrate these biomarkers in the clinical decision-making arsenal of physicians when considering the most appropriate clinical management.

REFERENCES

Throughout this application, various references describe the state of the art to which this invention pertains. The disclosures of these references are hereby incorporated by reference into the present disclosure.

1. Nankivell, B J, Borrows, R J, Fung, C L, O'Connell, P J, Allen, R D, Chapman, J R: The natural history of chronic allograft nephropathy. *The New England journal of medicine*, 349: 2326-2333, 2003.
2. Seron, D, Moreso, F, Bover, J, Condom, E, Gil-Vernet, S, Canas, C, Fulladosa, X, Torras, J, Carrera, M, Grinyo, J M, Alsina, J: Early protocol renal allograft biopsies and graft outcome. *Kidney international*, 51: 310-316, 1997.
3. Mannon, R B, Matas, A J, Grande, J, Leduc, R, Connett, J, Kasiske, B, Cecka, J M, Gaston, R S, Cosio, F, Gourishankar, S, Halloran, P F, Hunsicker, L, Rush, D, De, KAFI: Inflammation in areas of tubular atrophy in kidney allograft biopsies: a potent predictor of allograft failure. *Am J Transplant*, 10: 2066-2073, 2010.
4. Cosio, F G, Grande, J P, Wadei, H, Larson, T S, Griffin, M D, Stegall, M D: Predicting subsequent decline in kidney allograft function from early surveillance biopsies. *Am J Transplant*, 5: 2464-2472, 2005.
5. Mengel, M, Reeve, J, Bunnag, S, Einecke, G, Sis, B, Mueller, T, Kaplan, B, Halloran, P F: Molecular correlates of scarring in kidney transplants: the emergence of mast cell transcripts. *Am J Transplant*, 9: 169-178, 2009.
6. Park, W D, Griffin, M D, Cornell, L D, Cosio, F G, Stegall, M D: Fibrosis with inflammation at one year predicts transplant functional decline. *Journal of the American Society of Nephrology: JASN*, 21: 1987-1997, 2010.
7. Scherer, A, Gwinner, W, Mengel, M, Kirsch, T, Raulf, F, Szustakowski, J D, Hartmann, N, Staedtler, F, Engel, G, Klupp, J, Korn, A, Kehren, J, Haller, H: Transcriptome changes in renal allograft protocol biopsies at 3 months precede the onset of interstitial fibrosis/tubular atrophy (IF/TA) at 6 months. *Nephrology, dialysis, transplantation: official publication of the European Dialysis and Transplant Association—European Renal Association*, 24: 2567-2575, 2009.
8. Naesens, M, Khatri, P, Li, L, Sigdel, T K, Vitalone, M J, Chen, R, Butte, A J, Salvatierra, O, Sarwal, M M: Progressive histological damage in renal allografts is associated with expression of innate and adaptive immunity genes. *Kidney international*, 80: 1364-1376, 2011.
9. Thaunat, O, Legendre, C, Morelon, E, Kreis, H, Mamzer-Bruneel, M F: To biopsy or not to biopsy? Should we screen the histology of stable renal grafts? *Transplantation*, 84: 671-676, 2007.
10. Furness, P N, Philpott, C M, Chorbadjian, M T, Nicholson, M L, Bosmans, J L, Corthouts, B L, Bogers, J J, Schwarz, A, Gwinner, W, Haller, H, Mengel, M, Seron, D, Moreso, F, Canas, C: Protocol biopsy of the stable renal transplant: a multicenter study of methods and complication rates. *Transplantation*, 76: 969-973, 2003.
11. Gunther, O P, Balshaw, R F, Scherer, A, Hollander, Z, Mui, A, Triche, T J, Freue, G C, Li, G, Ng, R T, Wilson-McManus, J, McMaster, W R, McManus, B M, Keown, P A, Biomarkers in Transplantation, T: Functional genomic analysis of peripheral blood during early acute renal allograft rejection. *Transplantation*, 88: 942-951, 2009.
12. Flechner, S M, Kurian, S M, Head, S R, Sharp, S M, Whisenant, T C, Zhang, J, Chismar, J D, Horvath, S, Mondala, T, Gilmartin, T, Cook, D J, Kay, S A, Walker, J R, Salomon, D R: Kidney transplant rejection and tissue injury by gene profiling of biopsies and peripheral blood lymphocytes. *Am J Transplant*, 4: 1475-1489, 2004.
13. Sis, B, Mengel, M, Haas, M, Colvin, R B, Halloran, P F, Racusen, L C, Solez, K, Baldwin, W M, 3rd, Bracamonte, E R, Broecker, V, Cosio, F, Demetris, A J, Drachenberg, C, Einecke, G, Gloor, J, Glotz, D, Kraus, E, Legendre, C, Liapis, H, Mannon, R B, Nankivell, B J, Nickeleit, V, Papadimitriou, J C, Randhawa, P, Regele, H, Renaudin, K, Rodriguez, E R, Seron, D, Seshan, S, Suthanthiran, M, Wasowska, B A, Zachary, A, Zeevi, A: Banff '09 meeting report: antibody mediated graft deterioration and implementation of Banff working groups. *Am J Transplant*, 10: 464-471, 2010.
14. Chen, E Y, Tan, C M, Kou, Y, Duan, Q, Wang, Z, Meirelles, G V, Clark, N R, Ma'ayan, A: Enrichr: interactive and collaborative HTML5 gene list enrichment analysis tool. *BMC bioinformatics*, 14: 128, 2013.
15. Mengel, M, Reeve, J, Bunnag, S, Einecke, G, Jhangri, G S, Sis, B, Famulski, K, Guembes-Hidalgo, L, Halloran, P F: Scoring total inflammation is superior to the current Banff inflammation score in predicting outcome and the degree of molecular disturbance in renal allografts. *Am J Transplant*, 9: 1859-1867, 2009.
16. Scian, M J, Maluf, D G, Archer, K J, Suh, J L, Massey, D, Fassnacht, R C, Whitehill, B, Sharma, A, King, A, Gehr, T, Cotterell, A, Posner, M P, Mas, V: Gene expression changes are associated with loss of kidney graft function and interstitial fibrosis and tubular atrophy: diagnosis versus prediction. *Transplantation*, 91: 657-665, 2011.
17. Meas-Yedid, V, Servais, A, Noel, L H, Panterne, C, Landais, P, Herve, N, Brousse, N, Kreis, H, Legendre, C, Thervet, E, Olivo-Marin, J C, Morelon, E: New computerized color image analysis for the quantification of interstitial fibrosis in renal transplantation. *Transplantation*, 92: 890-899, 2011.
18. Loupy, A, Suberbielle-Boissel, C, Hill, G S, Lefaucheur, C, Anglicheau, D, Zuber, J, Martinez, F, Thervet, E, Mejean, A, Charron, D, Duong van Huyen, J P, Bruneval, P, Legendre, C, Nochy, D: Outcome of subclinical antibody-mediated rejection in kidney transplant recipients with preformed donor-specific antibodies. *Am J Transplant*, 9: 2561-2570, 2009.
19. Villeda, S A, Plambeck, K E, Middeldorp, J, Castellano, J M, Mosher, K I, Luo, J, Smith, L K, Bieri, G, Lin, K, Berdnik, D, Wabl, R, Udeochu, J, Wheatley, E G, Zou, B, Simmons, D A, Xie, X S, Longo, F M, Wyss-Coray, T: Young blood reverses age-related impairments in cognitive function and synaptic plasticity in mice. *Nature medicine*, 2014.
20. Mengel, M, Chang, J, Kayser, D, Gwinner, W, Schwarz, A, Einecke, G, Broecker, V, Famulski, K, de Freitas, D G, Guembes-Hidalgo, L, Sis, B, Haller, H, Halloran, P F: The molecular phenotype of 6-week protocol biopsies from human renal allografts: reflections of prior injury but not future course. *Am J Transplant*, 11: 708-718, 2011.
21. Vitalone, M J, O'Connell, P J, Wavamunno, M, Fung, C L, Chapman, J R, Nankivell, B J: Transcriptome changes of chronic tubulointerstitial damage in early kidney transplantation. *Transplantation*, 89: 537-547, 2010.

22. Maluf, D G, Mas, V R, Archer, K J, Yanek, K, Gibney, E M, King, A L, Cotterell, A, Fisher, R A, Posner, M P: Molecular pathways involved in loss of kidney graft function with tubular atrophy and interstitial fibrosis. *Molecular medicine,* 14: 276-285, 2008.
23. Condamine, T, Le Texier, L, Howie, D, Lavault, A, Hill, M, Halary, F, Cobbold, S, Waldmann, H, Cuturi, M C, Chiffoleau, E: Tmem176B and Tmem176A are associated with the immature state of dendritic cells. *Journal of leukocyte biology,* 88: 507-515, 2010.
24. Segovia, M, Louvet, C, Charnet, P, Savina, A, Tilly, G, Gautreau, L, Carretero-Iglesia, L, Beriou, G, Cebrian, I, Cens, T, Hepburn, L, Chiffoleau, E, Floto, R A, Anegon, I, Amigorena, S, Hill, M, Cuturi, M C: Autologous dendritic cells prolong allograft survival through tmem176b-dependent antigen cross-presentation. *American journal of transplantation: official journal of the American Society of Transplantation and the American Society of Transplant Surgeons,* 14: 1021-1031, 2014.
25. Viklicky, O, Krystufkova, E, Brabcova, I, Sekerkova, A, Wohlfahrt, P, Hribova, P, Wohlfahrtova, M, Sawitzki, B, Slatinska, J, Striz, I, Volk, H D, Reinke, P: B-cell-related biomarkers of tolerance are up-regulated in rejection-free kidney transplant recipients. *Transplantation,* 95: 148-154, 2013.
26. Zhang, Y, Zong, H T, Yang, C C, Zhang, X D: The clinical implication of inhibiting platelet activation on chronic renal allograft dysfunction: a prospective cohort study. *Transplantation proceedings,* 43: 2596-2600, 2011.
27. Sellares, J, de Freitas, D G, Mengel, M, Sis, B, Hidalgo, L G, Matas, A J, Kaplan, B, Halloran, P F: Inflammation lesions in kidney transplant biopsies: association with survival is due to the underlying diseases. *Am J Transplant,* 11: 489-499, 2011.
28. Zeeberg, B R, Feng, W, Wang, G, Wang, M D, Fojo, A T, Sunshine, M, Narasimhan, S, Kane, D W, Reinhold, W C, Lababidi, S, Bussey, K J, Riss, J, Barrett, J C, Weinstein, J N: GoMiner: a resource for biological interpretation of genomic and proteomic data. *Genome Biol,* 4, 2003.

The invention claimed is:

1. A method for adjusting the immunosuppressive treatment administered to a kidney transplant patient, wherein the method comprises the steps of:
  (i) determining the expression levels of bactericidal/permeability-increasing protein (BPI), chemokine (C motif) ligand 1 (XCL1) and thioredoxin domain containing 3 (TXNDC3) mRNAs in a blood sample obtained from a kidney transplant patient that is receiving an immunosuppressive treatment,
  (ii) comparing the expression levels of the BPI, XCL1 and TXNDC3 mRNAs in the blood sample with reference expression levels, wherein the reference expression levels are the levels of the BPI, XCL1 and TXNDC3 mRNAs in a blood sample from a subject that has a histologically normal kidney transplant,
  (iii) detecting a decrease in the expression levels of the BPI, XCL1 and TXNDC3 mRNAs in the blood sample compared to the reference expression levels, and
  (iv) adjusting the immunosuppressive treatment comprising providing a different amount of the immunosuppressive treatment or administering another immunosuppressive treatment to the kidney transplant patient.

2. The method according to claim 1, wherein the detected decrease in the expression levels of the BPI, XCL1 and TXNDC3 mRNAs is indicative of the presence of interstitial fibrosis and tubular atrophy (IFTA), inflammatory IFTA, or alloimmune lesions in the transplanted kidney.

3. The method according to claim 1, wherein said blood sample is obtained three months post-transplantation.

4. The method according to claim 1, wherein the immunosuppressive treatment at step (i) comprises a calcineurin inhibitor.

5. The method according to claim 1, wherein the immunosuppressive treatment at step (iv) comprises an mTOR inhibitor.

6. The method according to claim 1, wherein the blood sample is a whole blood sample, a serum sample, or a plasma sample.

7. The method according to claim 1, wherein the immunosuppressive treatment at step (i) comprises administration of cyclosporine to the subject.

8. The method according to claim 1, wherein the immunosuppressive treatment at step (iv) comprises administration of sirolimus or everolimus to the subject.

* * * * *